United States Patent [19]

Effenberger et al.

[11] Patent Number: 4,945,168
[45] Date of Patent: Jul. 31, 1990

[54] METHOD OF PREPARING ARYL-(1-PHTHALIMIDO)-ALKYL KETONES

[75] Inventors: Franz Effenberger, Stuttgart; Dieter Steegmüller, Magstadt, both of Fed. Rep. of Germany

[73] Assignee: Degussa Aktiengesellschaft, Frankfurt am Main, Fed. Rep. of Germany

[21] Appl. No.: 234,635

[22] Filed: Aug. 22, 1988

[30] Foreign Application Priority Data

Aug. 21, 1987 [DE] Fed. Rep. of Germany ....... 3727898

[51] Int. Cl.$^5$ .................. C07D 405/06; C07D 209/48
[52] U.S. Cl. ..................................... 548/454; 548/455; 548/461; 548/479
[58] Field of Search ................ 548/479, 454, 455, 461

[56] References Cited

U.S. PATENT DOCUMENTS 3,308,135   3/1967   Jansen et al. ................... 548/479

OTHER PUBLICATIONS

D. McClure et al., J. Organic Chemistry, vol. 48, No. 16, p. 2675 (1983).
L. Buckley, III et al., J. Am. Chem. Soc., vol. 103, p. 6157 (1981).
A. Hildesheimer, Ber. Dtsch. Chem. Ges., vol. 43, p. 2796 (1910).
S. Gabriel, Ber. Dtsch. Chem. Ges., vol. 44, p. 57 (1911).
R. Morrison et al., Organic Chemistry (second edition), p. 622 (1967), Allyn and Bacon, Inc., Boston.
Kirk–Othmer, Encyclopedia of Chemical Technology (second edition), vol. 10, p. 159 (1966), John Wiley and Sons, Inc.

Primary Examiner—Mary E. Ceperley
Attorney, Agent, or Firm—Cushman, Darby & Cushman

[57] ABSTRACT

Aryl-(1-phthalimido)-alkyl ketones of the general formula

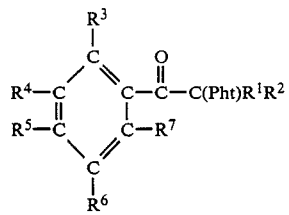

(I)

are prepared by reacting a suitable aromatic compound with

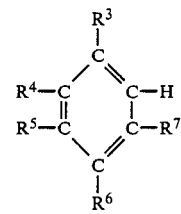

(II)

at least one hydrogen atom on the aromatic nucleus in an inert solvent and in the presence of iron-(III)-chloride with an N-phthaloyl-2-amino carboxylic acid chloride of the general formula

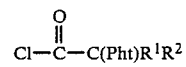

(III)

They can be converted into corresponding 2-phenethanolamines or 2-phenethylamines by reduction of the keto group.

3 Claims, No Drawings

METHOD OF PREPARING ARYL-(1-PHTHALIMIDO)-ALKYL KETONES

The present invention relates to a method of preparing aryl-(1-phthalimido)-alkyl ketones of the general formula

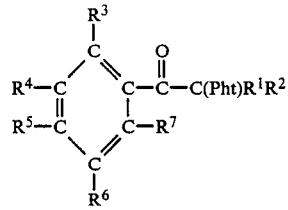

(I)

in which
$R^1$ signifies hydrogen or a straight-chain or branched $(C_1-C_4)$-alkyl group,
$R^2$ signifies hydrogen, a straight-chain or branched $(C_1-C_6)$-alkyl group, a benzyl group, a 4-$(C_1-C_4)$-alkoxy benzyl group, a 4-benzyloxylbenzyl group, a 3,4-di-$(C_1-C_4)$-alkoxybenzyl group, a 1,3-benzodioxol-5-yl-methyl group, an N-formyl-indole-3-yl-methyl group, an N-$(C_2-C_3)$-acylindole-3-yl-methyl group, a 5-$(C_1-C_4)$-alkoxy-N-$(C_2-C_3)$-acyl-indole-3-yl-methyl group, a 5-$(C_1-C_4)$-alkoxy-N-formyl-indole-3-yl-methyl group or a $(C_1-C_4)$-alkyl group substituted by a $(C_1-C_6)$-alkoxy group, a benzyloxy group, a phenyloxy group, a phthalimido group, a $(C_1-C_4)$-alkoxycarbonyl group or a benzyloxycarbonyl group,
$R^3$, $R^4$, $R^5$, $R^6$ and $R^7$ signify, independently of each other, hydrogen, a straight-chain or branched $(C_1-C_4)$-alkyl group, a $(C_1-C_6)$-alkoxy group, a benzyloxy group or a phenyloxy group and
Pht signifies a phthalimido group.

BACKGROUND OF THE INVENTION

Aryl-(1-phthalimido)-alkyl ketones are starting materials for the preparation of pharmacologically interesting active substances which are derived from 2-phenylethylamine. Thus, chiral 2-phenethanolamines or chiral 2-phenethylamines can be prepared by reduction of the keto group (JACS 103, 6157 [1981]).

The preparation of N-protected aryl-(1-amino)-alkyl ketones is normally performed by the Friedel-Crafts acylation of aromatic compounds with suitable, N-protected 2-amino carboxylic acid derivatives. However, attempts to acylate alkoxy-substituted aromatic compounds with N-protected 2-amino carboxylic acid chlorides a Friedel-Crafts reaction generally fail because of the complexing of aluminum chloride with the alkoxy substitutents and the deactivation of the aromatic compounds which this causes (JACS 103 6157 [1981]; J. Org. Chem. 48, 2675 [1983]).

SUMMARY OF THE INVENTION

The method of the present invention is characterized in that an aromatic compound of the general formula

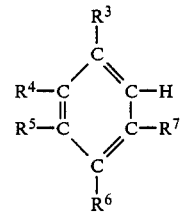

(II)

in which $R^3$, $R^4$, $R^5$, $R^6$ and $R^7$ each have one of the meanings already given, is reacted, in an inert solvent, and in the presence of iron-(III)-chloride with an N-phthaloyl-2-amino carboxylic acid chloride of the general formula

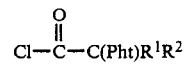

(III)

in which $R^1$, $R^2$ and Pht have the meanings already given.

Surprisingly, the reaction of alkoxy-substituted aromatic compounds is particularly successful with the method of the invention. Whereas, in customary Friedel-Crafts acylations, a onefold to threefold molar amount of aluminum chloride added must be used in relation to the acylating agent, very much smaller catalytic amounts of iron-(III)-chloride are sufficient in the method of the invention. The iron-(III)-chloride is preferably added in an amount between 0.5 and 50 mole percent in relation to the N-phthaloyl-2-amino carboxylic acid chloride of the general formula (III).

The reaction of the aromatic compound of the general formula (II) with the N-phthaloyl-2-amino carboxylic acid chloride of general formula (III) is carried out with advantage at a temperature in the range of −10° to 80° C.

Suitable inert solvents for carrying out the method of the invention are e.g. chlorinated aliphatic hydrocarbons such as methylene chloride, chloroform, carbon tetrachloride, 1,2-dichloroethane or trichloroethylene; alkanes such as hexanes, heptane or cyclohexane; and carbon disulfide.

A particularly advantageous embodiment of the method of the invention consists in that the N-phthaloyl-2-amino carboxylic acid chloride of general formula (III) is prepared in the inert solvent from the corresponding N-phthaloyl-2-amino carboxylic acid and then the iron-(III)-chloride and the aromatic compound of general formula (II) are added. The N-phthaloyl-2-amino carboxylic acid chloride of general formula (III) can be prepared e.g. by dissolving the corresponding N-phthaloyl-2-amino carboxylic acid in the inert solvent and converting it into the acid chloride with a reagent suitable for this purpose, e.g. phosphorus pentachloride. Then the iron-(III)-chloride and the aromatic compound of general formula (II) are added to the solution of N-phthaloyl-2-amino carboxylic acid chloride of general formula (III) obtained in this manner, and the mixture is agitated until the acid chloride is completely reacted. Alternatively, the solution of N-phthaloyl-2-amino carboxylic acid chloride of general formula (III) can also be introduced into a solution of iron-(III)-chloride and of the aromatic compound of general formula (II) placed in a receiver.

The reaction mixture is advantageously cooled down to 0° C. for workup and treated with saturated, aqueous sodium hydrogen carbonate solution or aqueous hydrochloric acid. The two phases which form are separated, and the organic phase is washed out with water. The aryl-(1-phthalimido)-alkyl ketone of general formula (I) formed is obtained in pure form by crystallization out of the organic phase or by known column-chromatographic method. The method of the invention has the advantage, when reacting chiral N-phthaloyl-2-amino carboxylic acid chlorides of general formula (III), that the reaction proceeds to a large extent with obtention of the center of chirality.

DETAILED DESCRIPTION OF PREFERRED EMBODIMENTS

The invention is illustrated in more detail by the following examples. The enantiomeric purity of the products obtained was demonstrated 1H-NMR-spectroscopically using the shift reagent Eu(hfbc)3.

EXAMPLE 1

A solution of 2.19 g (10.0 mmole) N-phthaloyl-(S)-alanine in 30 ml 1,2-dichloroethane was combined with 2.29 g (11.0 mmole) phosphorus pentachloride at 0° C. and agitated for 4 hours at room temperature. After the addition of 20 ml mesitylene and 16 mg iron-(III)-chloride (1 mole percent), the mixture was agitated for 48 hours at 25° C., then cooled down to 0° C. and treated with 50 ml saturated, aqueous sodium hydrogen carbonate solution and 20 ml acetone. The aqueous phase was separated off, and the organic phase was washed twice with 40 ml saturated, aqueous sodium hydrogen carbonate solution per wash. Then it was washed with water, and dried over sodium sulfate. After removal of the solvent at 40° C. under reduced pressure, the product crystallized when left standing in a refrigerator. It was dried over paraffin shavings. 2.54 g (79% of theory) (S)-2,4,6-trimethylphenyl-(1-phthalimidoethyl)-ketone of reagent purity with a melting point of 142°-143° C. were obtained.

$[\alpha]^{20}_D$: +52.8° (c=2, CHCl$_3$)

EXAMPLE 2

A solution of 2.61 g (10.0 mmole) N-phthaloyl leucine in 30 ml 1,2-dichloroethane was combined with 2.29 g (11.0 mmole) phosphorus pentachloride at 0° C. and agitated for 4 hours at room temperature. After the addition of 20 ml mesitylene and 16 mg iron-(III)-chloride (1 mole percent), the mixture was agitated at 50° C. for 40 hours, then cooled down to 0° C., mixed with 50 ml saturated, aqueous sodium hydrogen carbonate solution and 20 ml acetone and agitated for 4 hours at room temperature. The aqueous phase was separated off and extracted twice with 40 ml methylene chloride per extraction. The combined organic phases were washed with 40 ml saturated, aqueous sodium hydrogen carbonate solution, then with water, and dried over sodium sulfate. After removal of the solvent at 40° C. under reduced pressure, the product crystallized when left standing in a refrigerator. It was dried over paraffin shavings. 2.14 g (56% of theory) 2,4,6-trimethylphenyl-(3-methyl-1-phthalimidobutyl)-ketone of reagent purity with a melting point of 131°-132° C. were obtained.

EXAMPLE 3

A solution of 2.19 g (10.0 mmole) N-phthaloyl alanine in 30 ml 1,2-dichloroethane was combined with 2.29 g (11.0 mmole) phosphorus pentachloride at 0° C. and agitated for 4 hours at room temperature. After the addition of 20 ml p-xylene and 16 ml iron-(III)-chloride (1 mole percent), the mixture was agitated 48 hours at 25° C., then cooled down to 0° C., combined with 50 ml saturated, aqueous sodium hydrogen carbonate solution and 20 ml acetone and agitated for 4 hours at room temperature. The aqueous phase was separated off and extracted twice with 40 ml methylene chloride each time. The combined organic phases were washed with 40 ml saturated, aqueous sodium hydrogen carbonate solution, then with water, and dried over sodium sulfate. After removal of the solvent at 40° C. under reduced pressure, the product crystallized when left standing in a refrigerator. It was dried over paraffin shavings. 1.29 g (42% of theory) 2,4-dimethylphenyl-(1-phthalimidoethyl)-ketone of reagent purity with a melting point of 112° C. were obtained.

EXAMPLE 4

A solution of 4.38 g (20.0 mmole) N-phthalolyl-(S)-alanine in 120 ml 1,2-dichloroethane was combined with 4.58 g (22.0 mmole) phosphorus pentachloride at 0° C. and agitated for 4 hours at room temperature. After the addition of another 120 ml 1,2-dichloroethane, a tenth of the solution was rapidly added to an agitated solution of 3.32 g (20.0 mmole) hydroquinone diethylether and 320 mg iron-(III)-chloride (10 mole percent) in 80 ml 1,2-dichloroethane. The reaction mixture was heated to 50° C. and the remaining solution of acid chloride was added dropwise in a continuous manner within 12 hours. Then the mixture was agitated 12 hours further at 50° C. and then cooled down to 0° C. 100 ml 1N hydrochloric acid cooled down to 0° C. was added and the mixture agitated 24 hours at room temperature. The aqueous phase was separated off and extracted twice with 40 ml methylene chloride per extraction. The combined organic phases were washed with 150 ml saturated, aqueous sodium hydrogen carbonate solution and then with water. Then it was dried over sodium sulfate. After removal of the solvent at 40° C. under reduced pressure, the product was chromatographed over a silica gel column. After the solvent was removed again, the product crystallized when left standing in a refrigerator. 5.33 g (73% of theory) (S)-2,5-diethoxyphenyl-(1-phthalimidoethyl)-ketone with a melting point of 92°-93° C. were obtained.

$[\alpha]^{20}_D$: +25.9° (c=2, CHCl$_3$)

EXAMPLE 5

A solution of 2.61 g (10.0 mmole) N-phthaloyl leucine in 60 ml 1,2-dichloroethane was combined with 2.29 g (11.0 mmole) phosphorus pentachloride at 0° C. and agitated at first for 30 minutes at 0° C. and then for 4 hours at room temperature. After the addition of another 60 ml 1,2-dichloroethane, a tenth of the solution was rapidly added to an agitated solution of 1.66 g (10.0 mmole) hydroquinone diethylether and 160 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated for 12 hours further at 50° C. Then it was cooled down to 0° C. 100 ml 1N hydrochloric acid cooled down to 0° C. was added and the mixture agitated for 24 hours at room temperature. The aqueous phase was separated off and extracted twice with 20 ml methylene chloride per extraction. The combined organic phases were washed with 75 ml saturated, aqueous sodium hydrogen carbonate solution and then with water. It was dried over sodium sulfate. After removal of the solvent at 40° C. under reduced pressure, the product was chromatographed over a silica gel column. 2.53 g (62% of theory) 2,5-diethoxyphenyl-(3-methyl-1-phthalimidobutyl)-ketone of reagent purity were obtained as an oil.

EXAMPLE 6

A solution of 4.38 g (20.0 mmole) N-phthaloyl-(S)-alanine in 120 ml 1,2-dichloroethane was combined at 0° C. with 4.58 g (22.0 mmole) phosphorus pentachloride and agitated at first for 30 minutes at 0° C., then for 4 hours at room temperature. After the addition of another 120 ml 1,2-dichloroethane, a tenth of the solution was rapidly added to an agitated solution of 2.76 g (20.0 mmole) catechol dimethylether and 320 mg iron-(III)-chloride (10 mole percent) in 80 ml 1,2-dichloroethane. The reaction mixture was heated to 50° C. and the remaining solution of acid chloride was added dropwise in a continuous manner over 12 hours. Then the mixture was agitated 12 hours further at 50° C., then cooled down to 0° C. 100 ml 1N hydrochloric acid cooled down to 0° C. were added and the mixture agitated 24 hours at room temperature. The aqueous phase was separated off and extracted twice with 40 ml methylene chloride each time. The combined organic phases were washed with 150 ml saturated, aqueous sodium hydrogen carbonate solution, then with water, and dried over sodium sulfate. After removal of the solvent at 40° C. under reduced pressure, the product was recrystallized out of ethanol. 3.71 g (55% of theory) (S)-3,4-dimethoxyphenyl-(1-phthalimidoethyl)-ketone of reagent purity with a melting point of 126°–128° C. were obtained.

$[\alpha]^{20}_D$: −152.5° (c=1.2, CHCl$_3$)

EXAMPLE 7

A solution of 2.61 g (10.0 mmole) N-phthaloyl-(S)-leucine in 60 ml 1,2-dichloroethane was combined with 2.29 g (11.0 mmole) phosphorus pentachloride at 0° C. and agitated at first for 30 minutes at 0° C., then for 4 hours at room temperature. After the addition of another 60 ml 1,2-dichloroethane, a tenth of the solution was rapidly added to an agitated solution of 1.38 g (10.0 mmole) catechol dimethylether and 160 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated for 12 hours further at 50° C. and then cooled down to 0° C. 50 ml 1N hydrochloric acid, cooled down to 0° C., were added and the mixture agitated 24 hours at room temperature. The aqueous phase was separated off and extracted twice with 20 ml methylene chloride each time. The combined organic phases were washed with 75 ml saturated, aqueous sodium hydrogen carbonate solution, then with water. It was then dried over sodium sulfate. After removal of the solvent at 40° C. under reduced pressure, the product was chromatographed over a silica gel column. 2.11 g (55% of theory) (S)-3,4-dimethoxyphenyl-(3-methyl-1-phthalimidobutyl)-ketone of reagent purity with a melting point of 128.5° C. were obtained.

$[\alpha]^{20}_D$: −67.2° (c=1, CHCl$_3$)

EXAMPLE 8

A solution of 4.38 g (20.0 mmole) N-phthaloyl-(S)-alanine in 60 ml 1,2-dichloroethane was combined with 4.58 g (22.0 mmole) phosphorus pentachloride at 0° C. and agitated at first for 30 minutes at 0° C. and then for 4 hours at room temperature. After the addition of another 60 ml 1,2-dichloroethane, a tenth of the solution was rapidly added to an agitated solution of 2.16 g (20.0 mmole) anisole and 320 mg iron-(III)-chloride (10 mole percent) in 80 ml 1,2-dichloroethane. The reaction mixture was heated to 50° C. and the remaining solution of acid chloride was added dropwise in a continuous manner over 12 hours. The mixture was agitated 12 hours further at 50° C. and then cooled down to 0° C. 100 ml 1N hydrochloric acid cooled down to 0° C. were added and the mixture was agitated for 24 hours at room temperature. The aqueous phase was separated off and extracted twice with 40 ml methylene chloride per extraction. The combined organic phases were washed with 150 ml saturated, aqueous sodium hydrogen carbonate solution, then with water, and dried over sodium sulfate. After removal of the solvent at 40° C. under reduced pressure, the raw product was chromatographed over a silica gel column. The oily mixture of isomers obtained (4.56 g=74% of theory) was dissolved in hot toluene and the solution was compounded with n-hexane until cloudiness began. 2.14 g (35% of theory) (S)-4-methoxyphenyl-(1-phthalimidoethyl)-ketone of reagent purity with a melting point of 110° C. precipitated.

$[\alpha]^{20}_D$: −109.1° (c=2, CHCl$_3$)

EXAMPLE 9

A solution of 2.19 g (10.0 mmole) N-phthaloyl-(S)-alanine in 30 ml 1,2-dichloroethane was combined with 2.29 g (11.0 mmole) phosphorus pentachloride at 0° C. and agitated at first for 30 minutes at 0° C. and then for 4 hours at room temperature. After the addition of another 30 ml 1,2-dichloroethane, a tenth of the solution was rapidly added to an agitated solution of 1.22 g (10.0 mmole) ethoxybenzene and 160 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated for 12 hours further at 50° C. and then cooled down to 0° C. 50 ml 1N hydrochloric acid, cooled down to 0° C., were added and the mixture was agitated for 24 hours at room temperature. The aqueous phase was separated off and extracted twice with 20 ml methylene chloride per extraction. The combined organic phases were washed with 75 ml saturated, aqueous sodium hydrogen carbonate solution, then with water, and dried over sodium sulfate. The raw product was chromatographed over a silica gel column. 200 mg were separated from the oily mixture of isomers obtained (1.82 g=56% of theory) via MPLC. 50 mg (14% of theory) (S)-2-ethoxyphenyl-(1-phthalimidoethyl)-ketone of reagent purity was recovered as colorless oil {[$\alpha]^{20}_D$: +59.6° (c=1, CHCl$_3$)} as well as 96 mg (26% of theory) (S)-4-ethoxyphenyl-(1-phthalimidoethyl)-ketone of reagent purity as colorless oil {([$\alpha]^{20}_D$: −74° C. (c=2, CHCl$_3$)}.

EXAMPLE 10

A solution of 2.19 g (10.0 mmole) N-phthaloyl-(S)-alanine in 30 ml 1,2-dichloroethane was combined with 2.29 g (11.0 mmole) phosphorus pentachloride at 0° C. and agitated at first for 30 minutes at 0° C. and then for 4 hours at room temperature. After the addition of another 30 ml 1,2-dichloroethane, a tenth of the solution was rapidly added to an agitated solution of 1.50 g (10.0 mmole) n-butoxylbenzene and 160 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated for 12 hours further at 50° C. and then cooled down to 0° C. 50 ml 1N hydrochloric acid cooled down to 0° C. were added and the mixture was agitated for 24 hours at room temperature. The aqueous phase was separated off and extracted twice with 20 ml methylene chloride per extraction. The combined organic phases were washed with 75 ml saturated, aqueous sodium hydrogen carbonate solution, then with water, and dried over sodium sulfate. The raw product was chromatographed over a silica gel column. 170 mg were separated from the oily mixture of isomers obtained (2.01 g=57% of theory) via MPLC. 40 mg (13% of theory) (S)-2-butoxyphenyl-(1-phthalimidoethyl)-ketone of reagent purity was recovered as colorless oil {$[\alpha]^{20}_D$: +36.3° (c=0.8, CHCl$_3$)} as well as 64 mg (22% of theory) (S)-4-butoxyphenyl-(1-phthalimidoethyl)-ketone of reagent purity as colorless oil {$[\alpha]^{20}_D$: −63.2° C. (c=1.2, CHCl$_3$)}.

EXAMPLE 11

A solution of 2.47 g (10.0 mmole) N-phthaloyl-(S)-valine in 60 ml 1,2-dichloroethane was combined with 2.29 g (11.0 mmole) phosphorus pentachloride at 0° C. and agitated at first for 30 minutes at 0° C. and then for 4 hours at room temperature. After the addition of another 60 ml 1,2-dichloroethane, a tenth of the solution was rapidly added to an agitated solution of 1.38 g (10.0 mmole) catechol dimethylether and 160 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated for 12 hours further at 50° C. and then cooled down to 0° C. 50 ml 1N hydrochloric acid cooled down to 0° C. were added and the mixture was agitated for 24 hours at room temperature. The aqueous phase was separated off and extracted twice with 20 ml methylene chloride per extraction. The combined organic phases were washed with 75 ml saturated, aqueous sodium hydrogen carbonate solution, then with water, and dried over sodium sulfate. After removal of the solvent at 40° C. under reduced pressure, the product was chromatographed over a silica gel column. 2.16 g (59% of theory) (S)-3,4-dimethoxyphenyl-(2-methyl-1-phthalimidopropyl)-ketone of reagent purity were obtained as colorless oil.

$[\alpha]^{20}_D$: −200.4° (c=1, CHCl$_3$)

EXAMPLE 12

A solution of 4.06 g (10.0 mmole) N-N'-diphthaloyl-(S)-lysine in 60 ml 1,2-dichloroethane was combined with 2.29 g (11.0 mmole) phosphorus pentachloride at 0° C. and agitated at first for 30 minutes at 0° C. and then for 4 hours at room temperature. After the addition of another 60 ml 1,2-dichloroethane, a tenth of the solution was rapidly added to an agitated solution of 1.38 g (10.0 mmole) catechol dimethylether and 160 mg iron-(III)-chloride (10 mole percent) in 40 ml 1,2-dichloroethane. The reaction mixture was heated to 50° C., and the remaining solution of acid chloride was added dropwise in a continuous manner over 12 hours. The mixture Was agitated 12 hours further at 50° C. and then cooled down to 0° C. 50 ml 1N hydrochloric acid cooled down to 0° C. were added and the mixture agitated 24 hours at room temperature. The aqueous phase was separated off and extracted twice with 20 ml methylene chloride per extraction. The combined organic phases were washed with 75 ml saturated, aqueous sodium hydrogen carbonate solution, then with water, and dried over sodium sulfate. After removal of the solvent at 40° C. under reduced pressure, the product was chromatographed over a silica gel column. 3.26 g (62% of theory) (S)-3,4-dimethoxyphenyl-(1,5-bisphthalimidopentyl)-ketone of reagent purity with a melting point of 195° C. were obtained.

$[\alpha]^{20}_D$: −81.1° C. (c=1.1, CHCl$_3$)

EXAMPLE 13

A solution of 2.95 g (10.0 mmole) N-phthaloyl-(S)-phenyl alanine in 50 ml 1,2-dichloroethane was combined with 2.29 g (11.0 mmole) phosphorus pentachloride at 0° C. and agitated at first for 30 minutes at 0° C. and then for 16 hours at room temperature. After the addition of another 50 ml 1,2-dichloroethane, a tenth of the solution was rapidly added to an agitated solution of 1.38 g (10.0 mmole) catechol dimethylether and 160 mg iron-(III)-chloride (10 mole percent) in 70 ml 1,2-dichloroethane. The reaction mixture was heated to 50° C. and the remaining solution of acid chloride was added dropwise in a continuous manner over 12 hours. The mixture was agitated for 12 hours further at 50° C. and then cooled down to 0° C. 100 ml 1N hydrochloric acid, cooled down to 0° C., were added and the mixture agitated 24 hours at room temperature. The aqueous phase was separated off and extracted twice with 40 ml methylene chloride per extraction. The combined organic phases were washed with 150 ml saturated, aqueous sodium hydrogen carbonate solution, then with 100 ml water, and dried over sodium sulfate. After removal of the solvent at 40° C. under reduced pressure, the raw product was chromatographed over a silica gel column. 2.45 g (59% of theory) (S)-3,4-dimethoxyphenyl-(2-phenyl-1-phthalimidoethyl)-ketone of reagent purity were obtained as oil.

$[\alpha]^{20}_D$: −245° (c=1 CHCl$_3$)

0.25 g (9% of theory) 2-phthalimido-1-indanone of reagent purity with a melting point of 198°–199° C. was able to be isolated as byproduct.

EXAMPLE 14

A solution of 1.55 g (5.0 mmole) N-phthaloyl-2-methylphenyl alanine in 25 ml 1,2-dichloroethane was combined with 1.15 g (5.50 mmole) phosphorus pentachloride at 0° C. and agitated at first for 30 minutes at 0° C. and then for 16 hours at room temperature. After the addition of another 25 ml 1,2-dichloroethane, a tenth of the solution was rapidly added to an agitated solution of 0.69 g (5.0 mmole) catechol dimethylether and 80 mg iron-(III)-chloride (10 mole percent) in 40 ml 1,2-dichloroethane. The reaction mixture was heated to 50° C. and the remaining solution of acid chloride was added dropwise in a continuous manner over 12 hours. The mixture was agitated 12 hours further at 50° C. and then cooled down to 0° C. 50 ml 1N hydrochloric acid cooled down to 0° C. were added and the mixture was agitated for 24 hours at room temperature. The aqueous phase was separated off and extracted twice with 20 ml methylene chloride per extraction. The combined organic phases were washed with 75 ml saturated, aqueous sodium hydrogen carbonate solution, then with 50 ml water, and dried over sodium sulfate. After removal of the solvent at 40° C. under reduced pressure, the raw product was chromatographed over a silica gel column. 0.49 g (23% of theory) (S)-3,4-dimethoxyphenyl-(1-methyl-2-phenyl-1-phthalimidoethyl)-ketone of reagent purity with a melting point of 159°–161° C. were obtained.

0.15 g (10% of theory) 2-methyl-2-phthalimido-1-indanone of reagent purity with a melting point of 180° C. was able to be isolated as byproduct.

EXAMPLE 15

A solution of 3.25 g (10.0 mmole) N-phthaloyl-O-methyl-(S)-tyrosine in 50 ml 1,2-dichloroethane was combined with 2.29 g (11.0 mmole) phosphorus pentachloride at 0° C. and agitated at first for 30 minutes at 0° C. and then for 16 hours at room temperature. After the addition of another 50 ml 1,2-dichloroethane, a tenth of the solution was rapidly added to an agitated solution of 1.38 g (10.0 mmole) catechol dimethylether and 160 mg iron-(III)-chloride (10 mole percent) in 70 ml 1,2-dichloroethane. The reaction mixture was heated to 50° C. and the remaining solution of acid chloride was added dropwise in a continuous manner over 12 hours. The mixture was agitated 12 hours further at 50° C. and then cooled down to 0° C. 100 ml 1N hydrochloric acid cooled down to 0° C. were added and the mixture was agitated for 24 hours at room temperature. The aqueous phase was separated off and extracted twice with 40 ml methylene chloride per extraction. The combined organic phases were washed with 150 ml saturated, aqueous sodium hydrogen carbonate solution, then with 100 ml water, and dried over sodium sulfate. After removal of the solvent at 40° C. under reduced pressure, the raw product was chromatographed over a silica gel column. 1.93 g (43% of theory) (S)-3,4-dimethoxyphenyl-[2-(4-methoxyphenyl)-1-phthalimidoethyl]-ketone of reagent purity were obtained as oil.

$[\alpha]^{20}_D$: −245.2° (c=1, CHCl$_3$)

0.42 g (14% of theory) 6-methoxy-2-phthalimido-1-indanone of reagent purity with a melting point of 197°–199° C. was able to be isolated as byproduct.

What is claimed is:

1. A method of preparing aryl-(1-phthalimido)-alkyl ketones of the general formula

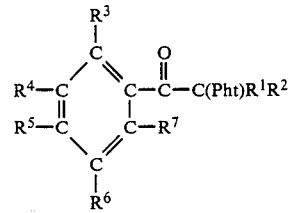

in which
R$^1$ signifies hydrogen or a straight-chain or branched (C$_1$–C$_4$)-alkyl group,
R$^2$ signifies hydrogen, a straight-chain or branched (C$_1$–C$_8$)-alkyl group, a benzyl group, a 4-(C$_1$–C$_4$)-alkoxy benzyl group, a 4-benzyloxybenzyl group, a 3,4-di-(C$_1$–C$_4$)-alkoxybenzyl group, a 1,3-benzodioxol-5-yl-methyl group, an N-formyl-indole-3-yl-methyl group, an N-(C$_2$–C$_3$)-acylindole-3-yl-methyl group, a 5-(C$_1$–C$_4$)-alkoxy-N-(C$_2$–C$_3$)-acyl-indole-3-yl-methyl group, a 5-(C$_1$–C$_4$)-alkoxy-N-formyl-indole-3-yl-methyl group or a (C$_1$–C$_4$)-alkyl group substituted by a (C$_1$–C$_6$)-alkoxy group, a benzyloxy group, a phenyloxy group, a phthalimido group, a (C$_1$–C$_4$)-alkoxycarbonyl group or a benzyloxy carbonyl group,
R$^3$, R$^4$, R$^5$, R$^6$ and R$^7$ signify, independently of each other, hydrogen, a straight-chain or branched (C$_1$–C$_4$)-alkyl group, a (C$_1$–C$_6$)-alkoxy group, a benzyloxy group or a phenyloxy group and
Pht signifies a phthalimido group,
which comprises reacting an aromatic compound of the general formula

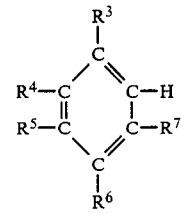

in which R$^3$, R$^4$, R$^5$, R$^6$ and R$^7$ each have one of the meanings already given is reacted in an inert solvent in the presence of iron-(III)-chloride with an N-phthaloyl-2-amino carboxylic acid chloride of the general formula

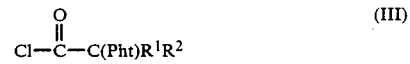

in which R$^1$, R$^2$ and Pht have the meanings already given wherein the iron-(III)-chloride is added in an amount between 0.5 and 50 mole percent in relation to the amount of N-phthaloyl-2-amino carboxylic acid chloride added.

2. A method as set forth in claim 1 in which the reaction is carried out at a temperature in a range of −10° to 80° C.

3. A method as set forth in claim 1 in which the N-phthaloyl-2-amino carboxylic acid chloride of general formula (III) is prepared in the inert solvent from the corresponding N-phthaloyl-2-amino carboxylic acid and then the iron-(III)-chloride and the aromatic compound of general formula (II) are added.

* * * * *